(12) United States Patent  
Scheiner

(10) Patent No.: US 7,606,619 B2
(45) Date of Patent: **\*Oct. 20, 2009**

(54) CONNECTION VERIFICATION APPARATUS, SYSTEMS, AND METHODS

(75) Inventor: Avram Scheiner, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 521 days.

This patent is subject to a terminal disclaimer.

(21) Appl. No.: 11/422,526

(22) Filed: Jun. 6, 2006

(65) Prior Publication Data

US 2006/0212083 A1 Sep. 21, 2006

Related U.S. Application Data

(63) Continuation of application No. 10/269,825, filed on Oct. 10, 2002, now Pat. No. 7,076,302.

(51) Int. Cl.
*A61N 1/00* (2006.01)

(52) U.S. Cl. ........................................ 607/27
(58) Field of Classification Search ................ 607/27, 607/28, 62, 63
See application file for complete search history.

(56) References Cited

U.S. PATENT DOCUMENTS

| | | | |
|---|---|---|---|
| 5,431,692 A * | 7/1995 | Hansen et al. | 607/28 |
| 5,534,018 A | 7/1996 | Wahlstrand et al. | |
| 5,741,311 A | 4/1998 | Mc Venes et al. | |
| 5,755,742 A | 5/1998 | Schuelke et al. | |
| 5,814,088 A | 9/1998 | Paul et al. | |
| 5,944,746 A | 8/1999 | Kroll | |
| 6,445,951 B1 | 9/2002 | Mouchawar | |
| 6,490,486 B1 * | 12/2002 | Bradley | 607/28 |
| 7,076,302 B2 | 7/2006 | Scheiner | |

OTHER PUBLICATIONS

ISO, "Cardiac defibrillators-Connector assembly DF-1 for implantable defibrillators-Dimensions and test requirements", *International Standard Organization*, ISO 11318: (2002) Second Edition (11318: 1993 has been withdrawn), (Aug. 1, 2002),27 pgs.
ISO, "Implants for Surgery-Cardiac Pacemakers- Part 3: Low-profile connectors [IS-1] for implantable pacemakers", *International Standard Organization*, ISO 5841-3: (2000) Second Edition, (Oct. 15, 2000),18 pgs.
"U.S. Appl. No. 10/269,825 Amendment and Response filed Oct. 5, 2005 to Office Action mailed Jul. 5, 2005", 9 pgs.
"U.S. Appl. No. 10/269,825, Non-Final Office Action mailed Jul. 5, 2005", 5 pgs.
"U.S. Appl. No. 10/269,825, Notice of Allowance mailed Feb. 23, 2006", 4 pgs.

* cited by examiner

*Primary Examiner*—Scott M Getzow
(74) *Attorney, Agent, or Firm*—Schwegman, Lundberg & Woessner, P.A.

(57) ABSTRACT

An apparatus, system, and method may operate to provide a connection signal using a first contact, measure a waveshape associated with a corresponding connection signal arising from the connection signal at a second contact connected to a first electrode using a lead, and provide a comparison result after determining whether the lead is a preselected lead type based on the waveshape.

25 Claims, 2 Drawing Sheets

CONNECTION VERIFICATION APPARATUS, SYSTEMS, AND METHODS

CROSS REFERNCE TO RELATED APPLICATION(S)

This application is a continuation of U.S. patent application Ser. No. 10/269,825, filed on Oct. 10, 2002, now U.S. Pat. No. 7,076,302 the specification of which is incorporated herein by reference.

TECHNICAL FIELD

Embodiments of the invention relate generally to measurement apparatus, systems, and methods, including those that operate to verify the correctness and integrity of electrical connections prior to operational use, including, for example, implanted cardiac leads connected to cardiac rhythm management devices.

BACKGROUND

During setup and implantation of cardiac rhythm management devices, including pacemakers, the attending physician typically connects one or more leads to a pulse generator, inserts the generator into the surgical pocket, and tests the system for proper operation. However, identification of correct lead connection and proper function can be time consuming and frustrating. This is due, in part, to the increased complexity of modern rhythm management devices.

Commonly available cardiac resynchronization systems include three leads, with up to eight electrodes. Advances in technology may increase the number of leads, electrodes, and sensors.

Connector standards, such as low voltage IS-1 (International Organization for Standardization (ISO) 5841-3:2000 Implants for Surgery—Cardiac Pacemakers—Part 3: Low-profile connectors (IS-1) for implantable pacemakers) and high voltage DF-1 (ISO 11318:1993 Cardiac Defibrillators—Connector Assembly DF-1 for implantable defibrillators—Dimensions and test requirements), have been established to differentiate and standardize various connector types. However, newer standards could operate to admit the use of connector ports having low voltage contacts (e.g., from about 1.0 volts to about 10.0 volts) intermixed with high voltage contacts (e.g., up to about 800 volts); such contacts may be substantially similar, or even identical, in appearance and dimensions.

Thus, newer standards, coupled with increased flexibility in rhythm management device design, could eventually permit a number of lead types to be connected to the same contact type within a port. Improper connections might be made more easily. However, if lead connection integrity and functionality were automatically verified prior to surgical closure, the efficacy of implantation operations could be improved.

SUMMARY

The apparatus, systems, and methods described herein provide the opportunity to detect incorrectly connected coronary leads and/or faulty connections to cardiac rhythm management devices in a more reliable manner. The approach involves injecting currents or impressing voltages over the available contact array, measuring several corresponding signals traveling through various leads, and determining whether the leads have been correctly connected, perhaps by comparing the measurements to a database of expected results. Improper connections can be directly indicated to the physician or other user.

An exemplary apparatus according to one embodiment of the invention may include a first contact (e.g., connected to a pacemaker can electrode) to provide a connection signal, a second contact (e.g., connected to a pacemaker lead and electrode) to sense the corresponding connection signal using the electrode coupled to the second contact, a measurement module coupled to the first and second contacts to measure a characteristic (e.g., a voltage or impedance) associated with the corresponding connection signal, a comparison module to determine whether the pacemaker lead is correctly connected, and an indicator module to indicate the comparison result.

A system according to various embodiments of the invention includes the apparatus coupled to a processor. The system may further include a voltage or current generator controlled by the processor.

A method according to various embodiments of the invention includes using a lead to connect an electrode to one contact, providing a connection signal from another contact, measuring a characteristic associated with the corresponding connection signal at the first contact, and determining a comparison result which indicates whether the lead is correctly connected. The method may also include indicating and recording the comparison result.

This summary is intended to provide an exemplary overview of the subject matter further described hereinbelow. It is not intended to provide an exhaustive or exclusive explanation of various embodiments of the invention. The Detailed Description which follows is included to provide further information about such embodiments.

DETAILED DESCRIPTION

Figure 1:
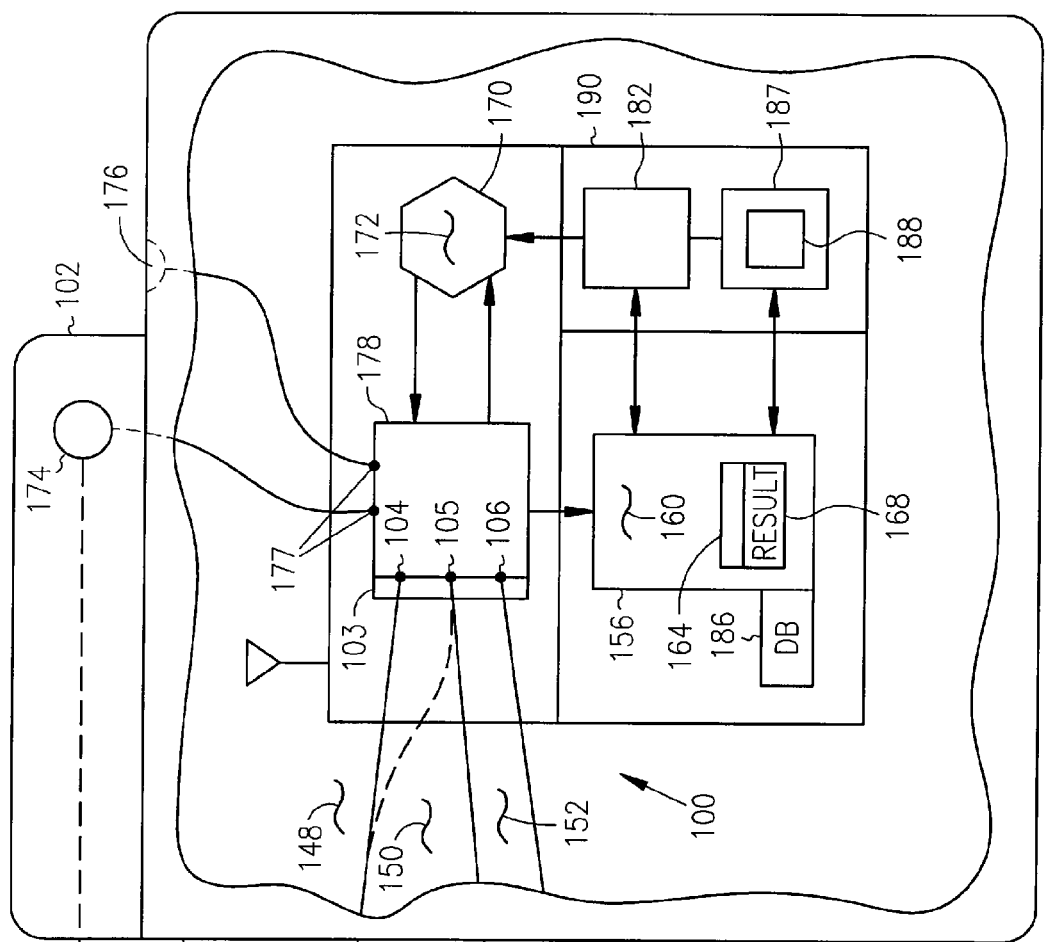
FIG. 1 is a schematic block diagram of an apparatus, and article, and a system according to various embodiments of the invention.
Figure 1:
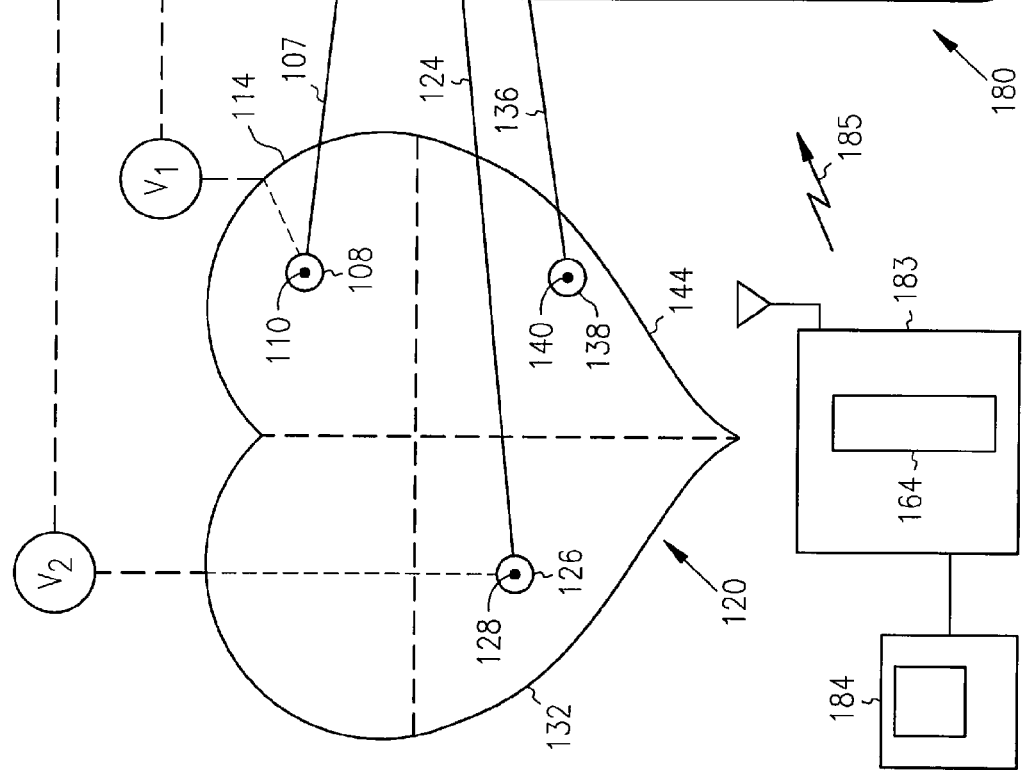

In the following detailed description of various embodiments of the invention, information with respect to making and using the various embodiments, including a best mode of practicing such embodiments, is provided. Thus, reference is made to the accompanying drawings which form a part hereof, and in which are shown by way of illustration, and not of limitation, specific embodiments in which the invention may be practiced. In the drawings, like numerals describe substantially similar components throughout the several views. The embodiments illustrated are described in sufficient detail to enable those skilled in the art to practice the teachings disclosed herein. Other embodiments may be utilized and derived therefrom, such that electrical, structural, and logical substitutions and changes may be made without departing from the scope of this disclosure. The following detailed description, therefore, is not to be taken in a limiting sense, and the scope of various embodiments of the invention is defined only by the appended claims, along with the full range of equivalents to which such claims are entitled.

It is understood that the embodiments described herein may relate to ventricular and/or atrial pacing therapy. Such embodiments may be applied to mammalian hearts, human and otherwise. The embodiments also include single chamber and dual chamber applications. It is also understood that the apparatus, systems, and methods provided herein are not limited to implantable devices, and may be used in devices external to the body. Additionally, other devices within and without the area of cardiac rhythm management may employ aspects of the various concepts presented herein without departing from the scope of various embodiments of the invention.

An apparatus to determine connection integrity and functionality measures characteristics associated with signals arising between two contacts included as part of a cardiac rhythm management device. By providing a mechanism to make impedance, timing, and other measurements, a comparison module and a database of expected results can be used to assess correct connection of multiple lead systems in a rapid and thorough manner.

FIG. 1 is a schematic block diagram of an apparatus, and article, and a system according to various embodiments of the invention. The apparatus 100, which may be included in a cardiac pacer unit 102, includes one or more ports 103. Each port, in turn, includes one or more contacts 104, 105, 106.

Leads can be used to attach electrodes to contacts. For example, a first contact 104 may be connected to one electrode of a first lead 107 (e.g. a right atrial (RA) lead 107 having an electrode pair, wherein the contact 104 is connected to either the RA ring electrode 108 or the RA tip electrode 110, disposed in the right atrium 114 of a heart 120) and a second contact 105 may be connected to the other electrode in the lead 107, or to an electrode included in a second lead 124 (e.g., a left ventricular (LV) lead 124, including an electrode pair, wherein the contact 105 is connected to either the LV ring electrode 126 or the LV tip electrode 128, disposed within the left ventricle 132). Additional contacts connected to various leads and electrodes may also be present, such as a third contact 106 connected to an electrode of a third lead 136 (e.g., a right ventricular (RV) lead 136, including an electrode pair, wherein the contact 106 is connected to either the RV ring electrode 138 or the RV tip electrode 140, disposed within the right ventricle 144).

Thus, any of the contacts 104, 105, and 106 can be connected to any of the electrodes 108, 110, 126, 128, 138, 140 via the leads 107, 124, 136, as desired by the architect of the apparatus 100. In addition, any number and type of signals 148, 150, and 152 (e.g., voltage or current) may be propagated from the contacts 104, 105, and 106 to the electrodes 108, 110, 126, 128, 138, 140, and vice-versa (i.e., from the electrodes to the contacts).

The apparatus 100 also includes a measurement module 156, capable of being communicatively coupled to the contacts 104, 105, and 106, and used to measure one or more characteristics of the signals 148, 150, and 152. Such characteristics include, but are not limited to, voltage, current, impedance, waveforms/waveshapes (e.g. sine, square, signatures, etc.), and/or time differentials. These characteristics can be affected by (or associated with) one or more of the leads 107, 124, 136 (e.g., the type of lead connected to the electrodes 108, 110, 126, 128, 138, and 140) and/or the communicating tissue and fluids situated therebetween (e.g., the heart 120, including one or more of its chambers). The apparatus 100 also includes a comparison module 164, and an indicator module 168.

A current injection device 170, such as a current generator 170, can be used to inject a current 172 between any lead electrode 108, 110, 126, 128, 138, 140 and any pacer electrode, such as a header electrode 174 or a can electrode 176, connected to contacts 177. A corresponding voltage V1, V2, arising between another lead electrode and another pacer electrode, can then be measured by the measurement module 156. Alternatively, voltages may be impressed across various combinations of electrodes, and the resulting currents (e.g., associated with signals 148, 150, 152) can be measured. Thus, each lead 107, 124, 136, including those associated with the electrode pairs 108, 110, 126, 128, 138, 140, is capable of propagating a current, injected or measured, and impressing or sensing a voltage. A switch 178 may be included in the apparatus 100 and used to control the distribution of injected current 172, as well as the acquisition of the resulting signals voltages V1, V2, among others.

Thus, for example, one contact 177, perhaps connected to a can electrode 176, can be used to provide a connection signal, such as a current 172, to a contact 104. Another contact, such as contact 105, can be used to sense a corresponding connection signal 150 using an electrode 126, 128 coupled to the contact 105, using the lead 124. The measurement module 156 can be used to measure one or more characteristics associated with the corresponding connection signal 150, such as its current, voltage, impedance, and/or time differential (i.e., the time difference of reception or propagation delay after launching the current pulse 172).

The comparison module 156 is used to determine, for example, whether the leads 107, 124, and 136 are correctly connected to the contacts 104, 105, and 106, respectively. In some embodiments, the determination can occur by comparing one or more measured characteristics (associated with the corresponding connection signals 148, 150, 152) with appropriate preselected ranges of values to provide a comparison result. Thus, for example, a lead 107 with a coated electrode 110 having a surface area of about 10 mm$^2$ would be expected to have an impedance of about 180 ohms to about 300 ohms. However, a lead 124 having a platinum-coated microtip electrode might be expected to present an impedance of about 1000 ohms to about 1400 ohms for proper operation. If the lead 107 was determined to have an impedance of about 1200 ohms, then the indication of the comparison result might be that the lead 107 was not of the preselected lead type (e.g., a lead having an expected impedance of about 180 to about 300 ohms).

Thus, an indication of a comparison result might include a measured impedance versus an expected impedance range. Another possibility, among many, is a conduction response time comparison result between the first and second electrodes. For example, if the atrium 114 is paced using the current 172, the measured response 152 in the ventricle 144 should occur within an expected range of about 120 milliseconds to about 180 milliseconds. Alternatively, an indication of the comparison result might simply be that the result was "correct" or "good", or "out of range" or the product of an "incorrect connection", or just "bad."

The indicator module 168 is used to indicate the result of the comparison, such as to a processor 182 and/or a pacer programmer 183. The result may be indicated on an indication device 184, such as a speaker 184 or display 184, coupled to, or included in the programmer 183. As shown in the figure, the comparison and/or indicator modules 164, 168 may be located within the apparatus 100, externally connected to the apparatus 100, or remotely, such as in the programmer 183. If such is the case, a wireless signal 185 may be used to communicate the measured characteristics 185, and/or the results of the comparison 185, and/or an indication of the results 185 between the apparatus 100 and the programmer 183.

A database module 186, located within the apparatus 100 externally, or remotely, such as in the programmer 183, is used to store a plurality of expected range values, including ranges of values selected to correspond to the leads 107, 124, and 136 connected to the apparatus 100. Manufacturers of various lead types, technicians, and physicians, among other users, may have periodic access to the database module 186 to update stored information as needed.

It may now be easily understood that the invention also includes a system 180, such as a cardiac rhythm management system 180, including the apparatus 100 described above, as well as a processor 182 capable of being communicatively coupled to the apparatus 100. The processor 182 may be coupled to a memory 187 containing data 188, such as program data, or data acquired via the measurement module 156. The processor 182 may be used to control various elements of the apparatus 100, such as the measurement module 156, the comparison module 164, the current injection device 170, and the switch 178.

As noted above, one or more contacts 104, 105, 106 can be coupled to one or more electrodes 108, 110, 126, 128, 138, 140. This includes coupling contacts to pacer electrodes, such as coupling a contact 177 to a pacer header electrode 174, or a pacer can electrode 176. Multiple contacts 104, 105, 106 can be included in a single port 103. The contacts may be different 104, 105, 106, substantially similar, or identical. Various characteristics associated with the measured signals 148, 150, 152 can be measured and compared, either to ranges of values stored in the database 186, and/or against each other. For example, the characteristic may be an impedance associated with a measured voltage of about 0.5 volts to about 10.0 volts. Or, as another example, the characteristic may be the conduction response time between two electrodes, ranging from about 50 milliseconds to about 250 milliseconds. Comparison results may indicate that all connections are correct, that incorrect connections exist between specific contacts and specific electrodes, and/or that certain leads are (or are not) of the expected type, etc.

It should be noted that current injection devices, and measured voltages have been used to illustrate specific embodiments of the invention. However, other embodiments may use voltage sources, combinations of voltage and current sources, measured currents and combinations of measured voltages and currents to arrive at the same result, which is the measurement of various signals from which characteristics leading to a determination of lead and electrode integrity and functionality can be reliably extracted.

The apparatus 100, the cardiac pacer unit 102, the contacts 104, 105, 106, the measurement module 156, the comparison module 164, the indicator module 168, the current injection device 170, the switch 178, the system 180, the processor 182, the programmer 183, the indication device 184, the database module 186, and the memory 187 may all be characterized as "modules" herein. Such modules may include hardware circuitry, and/or a processor and/or memory circuits, software program modules, and/or firmware, and combinations thereof, as desired by the architect of the apparatus 100 and the system 180, and as appropriate for particular implementations of various embodiments of the invention.

One of ordinary skill in the art will understand that the apparatus and systems of the present invention can be applied to systems other than those which include cardiac rhythm management devices, and thus, the invention is not to be so limited. The illustrations of an apparatus 100 and a system 180 are intended to provide a general understanding of the structure of the present invention, and they are not intended to serve as a complete description of all the elements and features of apparatus and systems that might make use of the structures described herein.

Applications that may include the novel apparatus and systems of the present invention include electronic circuitry used in communication and signal processing circuitry, modems, processor modules, embedded processors, and application-specific modules, including multilayer, multi-chip modules. Such apparatus and systems may further be utilized as sub-components within a variety of electronic systems, including cellular telephones, personal computers, radios, and others.

Figure 2:
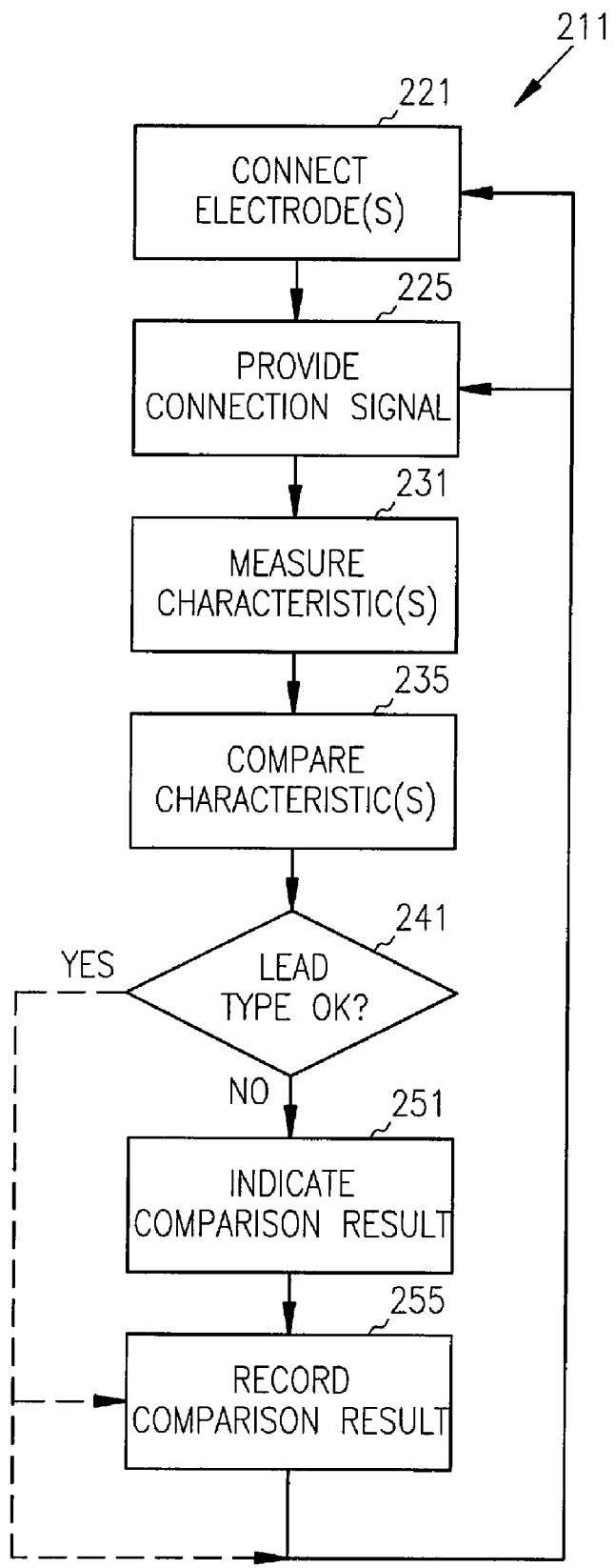
FIG. 2 is a flow diagram illustrating a method according to an embodiment of the invention.

FIG. 2 is a flow diagram illustrating a method according to an embodiment of the invention. The method 211 may begin with connecting one or more electrodes to one or more contacts at block 221 (e.g., by connecting one or more cardiac pacing leads to the contacts, such as an atrial lead having atrial tip and ring electrodes), and providing a connection signal, such as a current or voltage, using contacts other than the connected contact(s) at block 225 (such as a contact connected to a pacer can electrode). The method may continue with measuring one or more characteristics associated with the corresponding connection signal(s), appearing at the connected contact(s) arising from the provided connection signal at the contact at block 231. As noted above, characteristics may include a voltage (arising from an injected current connection signal), a current (arising from an impressed voltage connection signal), an impedance, a time differential on delay between the provided connection signal and the corresponding connection signal arising from the provided connection signal, etc.

The method may then continue with determining whether the pacing leads are of a preselected type, perhaps by comparing the measured characteristic(s) with one or more ranges of values to determine a comparison result at block 235. If the comparison result is such that the lead(s) are determined not to be of a preselected type, perhaps because the comparison result is not within the desired range (or even if the result is within the expected range, such that the lead connections have been properly made), the method may include indicating the comparison result at block 251. The method may then continue with recording the comparison result 255 in a memory included in the apparatus, the system, a programmer, or even within the database containing the ranges of values used for comparison. The method may then go back to block 221, wherein additional electrodes are connected, or to block 225, wherein additional connection signals are provided so that characteristics of other corresponding connection signals may be measured. Alternatively, if the comparison result is found to be within the range of values expected, the method may continue with block 221 or 225, or block 255, recording the comparison result.

Referring to the methods just described, it should be clear that some embodiments of the present invention may also be realized in the context of computer-executable instructions, such as program modules, being executed by a computer. Generally, program modules may include routines, programs, objects, components, data structures, etc. that perform particular tasks or implement particular abstract data types. As such, any of the modules 100, 102, 104, 105, 106, 156, 164, 168, 170, 178, 180, 182, 183, 184, 186, and 187 described herein may include software operative on one or more processors to perform methods according to the teachings of various embodiments of the present invention.

One of ordinary skill in the art will understand, upon reading and comprehending this disclosure, the manner in which a software program can be launched from a computer readable medium in a computer-based system to execute the functions defined in the software program. One of ordinary skill in the art will further understand the various programming languages that may be employed to create one or more software programs designed to implement and perform the methods disclosed herein. The programs can be structured in an objectorientated format using an object-oriented language such as Java, Smalltalk, or C++. Alternatively, the programs can be structured in a procedure-orientated format using a procedural language, such as COBOL or C. The software components may communicate using any of a number of mechanisms that are well-known to those skilled in the art, such as application program interfaces (API) or interprocess communication techniques such as the Remote Procedure Call (RPC). However, the teachings of various embodiments of the present invention are not limited to any particular programming language or environment.

As is evident from the preceding description, and referring back to FIG. 1, it can be seen that during the operation of the apparatus 100 a processor or control logic 182 may access some form of computer-readable media, such as the memory 187. Thus, a system 180 having an apparatus 100 according to an embodiment of the invention may also include a processor 182 coupled to a memory 187, volatile (e.g., Random Access Memory) or nonvolatile (e.g., a flash memory).

By way of example and not limitation, computer-readable media may comprise computer storage media and communications media. Computer storage media includes volatile and non-volatile, removable and non-removable media implemented in any method or technology for storage of information 188 such as computer-readable instructions, data structures, program modules or other data. Communications media specifically embodies computer-readable instructions, data structures, program modules or other data in a modulated data signal 185 such as a carrier wave 185, coded information signal 185, and/or other transport mechanism, which includes any information delivery media. The term "modulated data signal" means a signal that has one or more of its characteristics set or changed in such a manner as to encode information in the signal. By way of example and not limitation, communications media also includes wired media such as a wired network or direct-wired connections, and wireless media such as acoustic, optical, radio frequency, infrared and other wireless media. Combinations of any of the above are also included within the scope of computer-readable and/or accessible media.

Thus, it is now easily understood that another embodiment of the invention may include an article 190 comprising a machine-accessible medium or memory 187 having associated data 188, wherein the data 188, when accessed, results in a machine (e.g. the processor or control logic 182) performing activities such as providing a connection signal using a first contact (e.g., a current injected into the first contact connected to a can electrode), measuring a first characteristic (e.g. a voltage) associated with a corresponding connection signal arising from the provided connection signal at a second contact connected to another electrode (e.g., using a coronary lead), determining whether the lead is of a preselected type by comparing the first characteristic with a first range of values to determine a first comparison result, and indicating the first comparison result if the first characteristic is not within the first range of values. Other connection signals can be provided using the first contact, or other contacts and additional leads. Other characteristics associated with corresponding connection signals arising from the other provided connection signals can be measured so as to determine whether leads have been connected correctly (by determining whether leads are of an expected or preselected lead type). Such determinations may be accomplished by comparing appropriate ranges of values with the measured characteristics and used to determine comparison results (which can be indicated whether or not they fall within the expected ranges).

For example, assuming that a first contact is coupled to a pacer can electrode, a second contact is coupled to an atrial ring electrode, and a third contact is coupled to an atrial tip electrode, measuring a characteristic associated with the corresponding connection signal at the third contact may include measuring a voltage between the atrial tip electrode and the pacer can electrode after injecting a current between the atrial ring electrode and the pacer can electrode. These and other activities may be conducted during implantation activity, as well as during periodic checkups on the patient thereafter using a programmer and the various embodiments of the invention described above.

Although specific embodiments have been illustrated and described herein, those of ordinary skill in the art will appreciate that any arrangement which is calculated to achieve the same purpose may be substituted for the specific embodiments shown. This disclosure is intended to cover any and all adaptations or variations of various embodiments of the present invention. It is to be understood that the above Detailed Description has been made in an illustrative fashion, and not a restrictive one. Combinations of the above embodiments, and other embodiments not specifically described herein will be apparent to those of skill in the art upon reviewing the above description. The scope of various embodiments of the invention includes any other applications in which the above structures and methods are used. Therefore, the scope of various embodiments of the invention should be determined with reference to the appended claims, along with the full range of equivalents to which such claims are entitled.

It is emphasized that the Abstract is provided to comply with 37 C.F.R. §1.72(b) requiring an abstract that will allow the reader to quickly ascertain the nature of the technical disclosure. It is submitted with the understanding that it will not be used to interpret or limit the scope or meaning of the claims. It should also be noted that in the foregoing Detailed Description, various features may be grouped together in a single embodiment for the purpose of streamlining the disclosure. This method of disclosure is not to be interpreted as reflecting an intention that the claimed embodiments of the invention require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate preferred embodiment.

What is claimed is:

1. A method, including:
   connecting a first electrode to a second contact using a lead;
   providing a connection signal using a first contact coupled to a pacer electrode but not to the lead;
   measuring a waveshape associated with a corresponding connection signal arising from the connection signal at the second contact; and
   providing a comparison result after determining whether the lead is a preselected lead type based on the waveshape.

2. The method of claim 1, wherein connecting the first electrode includes:
   connecting the second contact to the lead comprising a cardiac pacing lead coupled to the first electrode.

3. The method of claim 1, including:
   indicating the comparison result.

4. The method of claim 1, including:
   recording the comparison result.

5. The method of claim 1, wherein the comparison result includes an indication that the first electrode is connected to the second contact using one of the preselected lead type and a lead type other than the preselected lead type.

6. An apparatus, including:
a first contact coupled to a pacer electrode but not to a lead;
a second contact;
a current injection module to provide a connection signal using the first contact;
a measurement module to couple to the first and the second contacts and to measure a waveshape of a corresponding connection signal propagated through the lead coupled to the second contact;
a comparison module to determine whether the lead is a preselected lead type based on the waveshape, and to provide a comparison result; and
an indicator module to indicate the comparison result.

7. The apparatus of claim 6, wherein the pacer electrode comprises a pacer can electrode.

8. The apparatus of claim 6, wherein the corresponding connection signal comprises a current.

9. The apparatus of claim 6, wherein the waveshape comprises a signature wave.

10. The apparatus of claim 6, including:
a database module having a preselected range of values corresponding to the preselected lead type.

11. A system, comprising:
an apparatus, including a first contact coupled to a pacer electrode but not to a lead, a second contact, a current injection module to provide a connection signal using the first contact, a measurement module to couple to the first and the second contacts and to measure a waveshape of a corresponding connection signal propagated through the lead coupled to the second contact, and a comparison module to determine whether the lead is a preselected lead type based on the waveshape, and to provide a comparison result; and
a processor to receive the comparison result.

12. The system of claim 11, wherein the pacer electrode is a pacer header electrode.

13. The system of claim 11, further including:
a display to couple to the processor and to indicate the comparison result.

14. The system of claim 11, further including:
a database module included in a pacer programmer to couple to the processor.

15. The system of claim 11, further including:
a programmer to couple to the apparatus using a wireless signal, and to receive an indication of the comparison result.

16. An article comprising a machine-accessible medium having associated instructions, wherein the instructions, when executed by the machine, result in a machine performing:
providing a connection signal using a first contact coupled to a pacer electrode but not to a lead;
measuring a waveshape associated with a corresponding connection signal arising from the connection signal at a second contact connected to a first electrode using the lead; and
providing a comparison result after determining whether the lead is a preselected lead type based on the waveshape.

17. The article of claim 16, wherein the second contact is coupled to an atrial ring electrode.

18. The article of claim 16, wherein the comparison result comprises an indication that the first electrode is connected to the second contact using a lead type other than the preselected lead type.

19. The article of claim 16, wherein the data, when accessed by the machine, results in the machine performing:
storing the comparison result in a database.

20. The method of claim 1, wherein the pacer electrode comprises a pacer header electrode.

21. The method of claim 1, wherein the pacer electrode comprises a pacer can electrode.

22. The apparatus of claim 6, wherein the pacer electrode comprises a pacer header electrode.

23. The system of claim 11, wherein the pacer electrode comprises a pacer can electrode.

24. The article of claim 16, wherein the pacer electrode comprises is a pacer header electrode.

25. The article of claim 16, wherein the pacer electrode comprises a pacer can electrode.

* * * * *

UNITED STATES PATENT AND TRADEMARK OFFICE
CERTIFICATE OF CORRECTION

PATENT NO. : 7,606,619 B2  Page 1 of 1
APPLICATION NO. : 11/422526
DATED : October 20, 2009
INVENTOR(S) : Avram Scheiner It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 657 days.

Signed and Sealed this

Twelfth Day of October, 2010

David J. Kappos
*Director of the United States Patent and Trademark Office*